United States Patent [19]

Hübner

[11] Patent Number: 4,585,667
[45] Date of Patent: Apr. 29, 1986

[54] PROCESS FOR PRODUCING PLASTER MODELS FOR USE IN DENTISTRY

[75] Inventor: Heijo Hübner, Wörthsee, Fed. Rep. of Germany

[73] Assignee: ESPE Fabrik Pharmazeutischer Praparate GmbH, Seefeld/Oberbayern, Fed. Rep. of Germany

[21] Appl. No.: 687,563

[22] Filed: Dec. 28, 1984

[30] Foreign Application Priority Data

Dec. 30, 1983 [DE] Fed. Rep. of Germany ....... 3347646

[51] Int. Cl.$^4$ .......................... A01N 1/02; B05D 3/06
[52] U.S. Cl. ........................................ 427/2; 427/53.1; 427/54.1; 433/213
[58] Field of Search ..................... 106/35; 427/2, 53.1, 427/54.1; 433/213

[56] References Cited

FOREIGN PATENT DOCUMENTS 0073995 3/1983 European Pat. Off. .............. 106/35

Primary Examiner—Michael B. Lusignan
Attorney, Agent, or Firm—Birch, Stewart, Kolasch & Birch

[57] ABSTRACT

The physical properties, especially resistance to abrasion, to bending and to pressure, of plaster models for use in dentistry are improved in that a plaster model obtained in a manner known in the art is impregnated with (a) at least one photopolymerizable ester of acrylic and/or methacrylic acid, (b) at least one photopolymerization initiator, and (c) optionally at least one photopolymerization activator—(a), (b) and (c) being present in liquid or dissolved state—and the impregnated plaster model is irradiated with light suitable to initiate photopolymerization by the photoinitiator.

16 Claims, No Drawings

PROCESS FOR PRODUCING PLASTER MODELS FOR USE IN DENTISTRY

BACKGROUND AND SUMMARY OF THE INVENTION

The present invention relates to a process for producing plaster models for use in dentistry by treating a plaster model obtained in a manner known in the art with polymerizable esters of acrylic and/or methacrylic acid and polymerization initiators. and polymerizing the monomers.

Plaster models used in dentistry, e.g. models of natural dentures permitting the integration of artificial teeth or orthodontic devices in the dental laboratory, are subject to numerous operations. The resulting wear causes abrasion of the plaster surface, which may significantly affect the exact fit of the workpiece in the mouth. If workpieces fit too tightly, it may happen that the tooth stump to be jacketed breaks off when the crown is removed. In this way the entire denture model may become useless, so that the operation of making an impression and a casting must be repeated. In order to fit the denture parts into a natural set of teeth, the plaster model is frequently placed in a so-called articulator which simulates the movement of the jaws and wherein the plaster model comes into contact with the plaster model of the respective other jaw. Careless opening and closing of the articulator can cause abrasion in the respective opposite row of teeth. Also, sometimes small particles of the antagonist teeth break off, which jeopardizes the precise fit of the workpiece in the mouth.

The properties and problems of commercial materials for dental models are described in Deutsche Zahnarztliche Zeitung, Vol. 32, pages 937-941 and 942-944 (1977).

For some time the so-called super-hard plasters have been known which exhibit improved resistance to abrasion and/or to pressure and bending. However, in most cases only one of said properties is improved while the other properties remain unsatisfactory. Moreover, these plasters are very expensive and are frequently difficult to process.

There have been attempts to improve the properties of plaster models by application of solvent-based drying lacquers (Deutsche Offenlegungsschrift No. 3,009,755). However, it has been found that the properties of the models can be improved only slightly. Moreover, there is the risk of a dimensional change in the model, due to the application of the lacquer and the rapid evaporation of the solvent, before the solution has penetrated into the plaster.

There also have been attempts to improve the properties of plaster models by means of cyanacrylates (Journ.Prost.Dent., Vol. 49, page 639, (1983)). However, rapid curing with water renders this method unsafe, because the penetration of the cyanacrylate into the plaster becomes uncontrollable. Moreover, the handling of cyanacrylates involves safety hazards.

From European Patent Publication No. 0,013,354 it has become known to treat the surface of plaster models with autopolymerizing compositions. However, this can lead to uncontrolled dimensional changes of the plaster model; also the physical properties are improved only slightly, because the rapidly polymerizing composition penetrates into the plaster only to a very limited extent.

Hence, it is the object of the present invention to modify the process for producing plaster models for use in dentistry, in which a plaster model is treated with polymerizable esters of acrylic and/or methacrylic acid and polymerization initiators and the monomers are polymerized. As a result, the physical properties of the plaster models, especially the resistance to abrasion and to bending and pressure is improved and the process can be carried out simply and in a minimum of time with minimum costs.

According to the present invention, this object is realized by impregnating a plaster model obtained in a manner well known in the art with (a) at least one photopolymerizable ester of acrylic and/or methacrylic acid, (b) at least one photopolymerization initiator, and (c) optionally at least one photopolymerization activator, the components (a), (b) and (c) being present in a liquid or dissolved state, and the impregnated plaster model is irradiated with light suited for initiating the photopolymerization by the photoinitiator.

The components (a), (b), and (c) can be applied simultaneously or in succession.

According to a preferred embodiment, the components (b) and/or (c) can be employed in the form of a mixture with at least a portion of (a).

The viscosity of the components (a), (b), (c), the mixtures or solutions thereof is preferably $\leq 5$ poises, preferably $<1$ poise.

With the process of the present invention there are obtained in a manner requiring little time and at low costs, plaster models with significantly improved resistance to abrasion, pressure and bending, without an appreciable change in the dimension of the models. Variations in the characteristics due to variations in the plaster/water ratio employed and in the mixing technique, which frequently occur in practice, are substantially eliminated by the process of the present invention. The process of the present invention provides a model highly resistant to abrasion, pressure, and bending from a model made of a blend of inferior quality.

For the process of the present invention plaster models made from any desired types of plaster suited for use in dentistry can be employed. The types of plaster employed substantially consist of calcium sulphate; they may contain additives for imparting more favorable properties to the plaster model, e.g. better setting behavior or greater hardness. The basic chemistry of dental plasters is described in "Ullmanns Encyclopadie der technischen Chemie", 4th edition, Vol. 10, page 19 (1975). However, depending on the type of photoinitiator (b) employed the plaster must not exhibit any light absorption in the range of from 250 to 500 nm or high enough to adversely affect the polymerization. Preferably the plaster has only low light absorption values in said range. Undyed plasters are especially preferred.

The so-called urethane acrylates and methacrylates come into consideration as photopolymerizable esters of acrylic and methacrylic acid which can be utilized in the present invention.

The urethane acrylates and methacrylates are obtained in a known manner by reaction of isocyanates and hydroxyalkylacrylates or methacrylates. It is also possible to react hydroxyl compounds with one equivalent of a diisocyanate, and to then react the resulting isocyanate compounds with hydroxyalkylacrylates or methacrylates to form the urethane acrylates or methacrylates. Suitable products are commercially available by the tradename "Genomer".

Monofunctional as well as di- or polyfunctional acrylates and methacrylates may be employed. Preferably the proportion of monofunctional acrylate and/or methacrylate comprises from 0 to 70% by weight of component (a). Methyl methacrylate and hydroxyethyl methacrylate are especially preferred monofunctional derivatives.

Suitable photopolymerization initiators are all the substances known for the photopolymerization of derivatives of acrylic and methacrylic acid, such as aromatic monoketones, thioxanthones, aromatic and aliphatic 1,2-diketones, benzoine ethers and benzil ketals.

Among the above mentioned photoinitiators the 1,2-diketones have proved to be particularly effective. In order to prevent a tacky surface of the polymer caused by the inhibitive effect of atmospheric oxygen, a combination of several photoinitiators is preferably employed whose active light absorption becomes effective at different wavelengths. A combination of benzophenone (active absorption at about 255 nm and about 345 nm), benzil dimethylketal (active absorption at about 360 nm), and camphor quinone (active absorption at about 460 nm) or phenanthrene quinone (active absorption at about 420 nm) is especially well suited.

The photoinitiators are employed in the customary concentrations, i.e. 0.01 to about 3% by weight, based on the component (a).

Advantageously, the photoinitiators are used together with known photoactivators. Suitable photoactivators are organic amines, especially tertiary amines, cyclic 1,3-diketones, such as barbituric acids and 2-substituted 1,3-cyclopentanediones and 1,3-cyclohexanediones, and organic phosphites.

Optionally volatile solvents, such as methylene chloride, can be added to the components (a), (b), (c) or mixtures thereof in order to reduce the viscosity. Hydrophilic solvents, such as acetone, are preferred, which at the same time permit faster penetration into fresh, moist plaster models. The viscosity of the mixtures can also be adjusted by the use of monofunctional methacrylates in suitable concentrations. The use of hydrophilic methacrylates (up to 50% by weight of the component (a)) is desirable, because in this way better penetration of the component (a) or a mixture thereof with (b) and/or (c) into the moist plaster model is achieved. Suitable hydrophilic methacrylates are hydroxyalkyl methacrylates, especially 2-hydroxyethyl methacrylate and 3-hydroxypropyl methacrylate.

In order to achieve better film formation, or optionally to increase the viscosity, soluble polymers can be added to the components (a), (b) and/or (c).

Also the addition of surface-active substances is possible to improve the penetration of (a), (b) and/or (c) into the plaster model. For this purpose hydrophilic sorbimacrogols are suitable.

The components (a), (b), and/or (c) can also be dyed with suitable dyestuffs. However, the dyestuffs must be selected so that they do not have a high independent absorption in the range in which the photoinitiators employed exhibit their active light absorption. When photoinitiators for the visible range are employed (e.g. camphor quinone, active absorption at 400 to 500 nm), the selected dyestuffs may exhibit only slight independent absorption between 400 and 500 nm.

It is possible to use, in addition to the photoinitiator, (d) an organic peroxide or hydroperoxide and (e) an activator therefor, such as aromatic amines or thiourea derivatives, which are blended before use. The concentrations of (d) and (e) must be so selected that, after blending of (d), (e), and the other components, the polymerization takes place only after several minutes, in order to achieve deep penetration of the component (a) into the plaster. Preferably the polymerization, in this case, should begin not earlier than 5 minutes after blending of (d) and (e) with the other components. In this way deeper strata can be cured, which are not accessible to polymerization by the action of light alone.

The components (a), (b), (c), (d) and (e) or mixtures thereof, can be applied on the plaster model utilizing conventional measures in one or several applications, such as for example, spraying, dipping, or application with a brush. Preferably the plaster model is immersed for a period of from 3 to 15 minutes, with immersion periods of 7 to 10 minutes being particularly suitable. The minimum penetration depth of component (a) into the plaster model is preferably 0.1 mm, preferably at least 0.5 mm.

For irradiation of impregnated plaster models, conventional lamps can be employed, as long as they provide sufficient radiation in the wavelength range which corresponds to the active light absorption range of the photoinitiator (b) employed. Xenon lamps, mercury lamps operating at low, medium and high pressure, halogen lamps and fluorescent lamps, and combination of such lamps, can be used. Preferably fluorescent lamps are employed, because they develop only little heat and do not require expensive cooling measures.

The irradiation periods may vary between a few minutes and several hours, depending on the intensity of the light source. With the use of fluorescent lamps the irradiation periods typically range between 15 minutes and 1 hour. In order to obtain a dry surface of the polymer, the inhibition by atmospheric oxygen must be overcome. This can be achieved by radiation in the range between 250 and 370 nm together with a photoinitiator whose active light absorption is within the indicated range. Preferably a mixture of benxophenone and benzil dimethylketal is used as the photoinitiator, in combination with a fluorescent lamp emitting at about 250 nm and a second fluorescent lamp emitting at about 360 nm, as the light source.

Alternatively, the inihibition of oxygen can be overcome also by the use of a protective gas such as nitrogen, carbon, dioxide, or argon. The protective gases can be used at normal or at superatmospheric pressure. Polymerization in a vacuum to eliminate atmospheric oxygen is less suitable, because water contained in the plaster will form bubbles, and some vacuum pumps might be damaged by the evolving water vapor. The activity of atmospheric oxygen can also be reduced by application of a protective film of wax or glycerol, for example.

In order to achieve good, deep polymerization, the use of visible light in the spectral range of 400 to 500 nm, in addition to the two above mentioned types of light, is advantageous, together with a fluorescent lamp preferably 1,2-diketones are employed as photoinitiators—camphor quinone and phenanthrene quinone being especially suited, optionally in combination with an amine as photoactivator.

The following Examples are given as being exemplary of the present invention and accordingly should not be considered as limiting the scope of the present invention.

EXAMPLES

The following photopolymerizable formulations are prepared:

Solution A
- 1.00 gram benzophenone
- 0.10 gram benzil dimethylketal
- 0.06 gram camphor quinone, and
- 0.30 gram methyl diethanolamine dimethacrylate are dissolved in a mixture of
- 5.00 grams methyl methacrylate and
- 15.00 grams bis-hydroxymethyl-bicyclo [5.2.1.0$^{2.6}$] decanediacrylate.

Solution B
- 1.00 gram benzophenone
- 0.10 gram benzil dimethylketal, and
- 0.004 gram phenanthrene quinone are dissolved in a mixture of
- 5.00 grams methyl methacrylate and
- 15.00 grams bis-hydroxymethyl-bicyclo [5.2.1.0$^{2.6}$] decanediacrylate.

Solution C
- 0.20 gram sorbimacrogol laurate (tradename "Tween 20") is dissolved in
- 10.5 grams of solution B.

Solution D
- 1.00 gram benzophenone
- 0.10 gram benzil dimethylketal
- 0.06 gram camphor quinone, and
- 0.30 gram methyl diethanolamine dimethacrylate are dissolved in a mixture of
- 6.67 gram bis-hydroxymethyl-bicyclo[5.2.1.0$^{2.6}$] decanediacrylate
- 6.67 grams methyl methacrylate, and
- 6.67 grams 2-hydroxyethyl methacrylate.

Solution E
- 0.25 gram sorbimacrogol laurate (tradename "Tween 20") is dissolved in
- 5.00 grams of solution D.

Solution F
- 1.00 gram benzophenone
- 0.10 gram benzil dimethylketal and
- 0.004 gram phenanthrene quinone are dissolved in
- 20.00 grams of bis-hydroxymethyl-bicyclo[5.2.1.0$^{2.6}$] decanediacrylate.

Solution G
- 1.00 gram benzophenone
- 0.10 gram benzil dimethylketal
- 0.06 gram camphor quinone and
- 0.30 gram methyl diethanolamine dimethacrylate are dissolved in a mixture of
- 10.00 grams of trifunctional aliphatic urethane-/polyester acrylate (theoretical average molecular weight 1600, tradename "Genomer T 1600" of Messrs. Rahn) and
- 10.00 grams of methyl methacrylate.

The resulting solutions are filled into a light-tight oxygen-permeable bottle (e.g. black polypropylene bottle) wherein they are storable.

EXAMPLE 1

A master model of a commercial hard plaster (marketed by Messrs. Kerr under the tradename "Vel-Mix-Stone") for dental prosthetic work is obtained, as usual by filling the dental impression of the jaw part. According to methods known in the art, the model is removed from the mold after about 30 minutes and allowed to harden for 24 hours.

Solution A is applied to the tooth stumps of the plaster model by means of a fine brush. After a short time (about 1 to 2 minutes) all of the solution has penetrated into the plaster and the initially glossy surface has turned dull again. The application of the solution is repeated (3 to 4 times) until a glossy film remains on the tooth stump. The film is carefully removed with a lint-free absorptive cloth.

The pretreated model is then placed into an exposure apparatus containing 3 fluorescent tubes and is left there for 20 minutes. The intensity maxima of the three tubes is 255 nm, 360 nm, and 460 nm, respectively.

After the irradiation, a plaster model whose stumps are exactly fitting and are resistant to abrasion and rupture is obtained.

EXAMPLE 2

Solution B is cast into a bowl, and a plaster model obtained as described in Example 1 with the stumps and the remaining teeth is immersed into the solution for 7 minutes.

After removal from the solution, the immersed parts are carefully freed from the remaining liquid film with pressurized air. Thereafter the model is exposed to light, as described in Example 1.

There is obtained a plaster model with teeth, stump and jaw portions showing a high resistance to abrasion and rupture.

Comparable results are obtained with the use of the solutions F and G in lieu of solution B.

EXAMPLE 3

A plaster model obtained according to Example 1 is treated with solution C as described in Example 1, two hours after removal from the mold. The solution is readily absorbed by the moist plaster. After irradiation with the lamp mentioned in Example 1 for 20 minutes, a model whose stumps exhibit high flexural and abrasion resistance is obtained.

EXAMPLE 4 (COMPARATIVE TEST)

In a sclerometric test according to Martens the specific sclerometric volume loss per 1 cm test length is determined.

To this end a commercial dental hard plaster (tradename "Moldano" supplied by Bayer) is cast in panels of 25 mm × 25 mm × 2 mm. After adequate aging of the test panels, a steel needle having a cone angle of 90° is applied under a load of 10 N. Said needle is drawn across the plaster by way of a motor-driven eccentric disk along a length of about 2 cm. The width of the cut produced by the steel needle is determined under the measuring microscope, and therefrom the specific volume loss per 1 cm length is calculated.

In the following table the sclerometric volume losses are recorded for the untreated plaster panel, and for the test panels treated according to Example 1 with the solutions A, D and E. Each test was carried out with plaster which had been stored prior to the measurement for a period of 1 hour, 2 hours, and 1 week in a standard climate (23±1° C.; 45−5% relative humidity).

TABLE 1

| Storage of Plaster in Standard Climate | Treatment | Specific Sclerometric Volume Loss per 1 cm Groove Length [mm$^3$ × 10$^{-3}$] |
|---|---|---|
| 1 hour | none | 1140 |
|  | solution A | 480 |

TABLE 1-continued

| Storage of Plaster in Standard Climate | Treatment | Specific Sclerometric Volume Loss per 1 cm Groove Length [mm³ × 10⁻³] |
|---|---|---|
| | solution D | 300 |
| | solution E | 200 |
| 2 hours | none | 470 |
| | solution A | 150 |
| | solution D | 83 |
| | solution E | 76 |
| 1 week | none | 225 |
| | solution A | 69 |
| | solution D | 51 |
| | solution E | 51 |

At all times during plaster hardening the process of the present invention offers an improvement in the abrasion resistance of at least about 3 times.

Already 2 hours after the preparation of a plaster model, abrasion resistance values are obtained which are far superior to that of completely hardened plaster. Also, in completely hardened plaster the process of the present invention reduces abrasion about $\frac{1}{3}$ to $\frac{1}{4}$.

From Table 1 it is apparent that hydrophilic additives are active, especially in fresh, moist plaster, while in dry plaster the differences are slight.

EXAMPLE 5 (COMPARATIVE TEST)

In the manner described in Example 4 test panels were produced from a commercial hard plaster (tradename "Duroc" of Ransom and Randolph) and the specific sclerometric volume loss was determined for the untreated plaster panel, for plaster panels treated according to the prior art, and for a plaster panel treated according to the present invention (Table 2).

Moreover, from the produced test panels standard pieces measuring 2 mm×2 mm×25 mm for the DIN 13922 bending test. In the procedure following the present invention those pieces were immersed into the solution A for 7 minutes, the excess was removed as described in Example 2, and the samples were exposed to light as described in Example 1. The prior art materials were applied with a brush according to the manufacturer's instructions, and dried accordingly.

TABLE 2

| Curing Solution | Specific Sclero-Volume Loss per 1 cm Groove Length [mm³ × 10⁻³] | Bending Strength [MPa] |
|---|---|---|
| none | 245 | 19.0 |
| polymethyl methacrylate in acetone (tradename "Almadent Gipsversiegelung") (prior art) | 235 | 19.2 |
| tradename "Bego Stumpflack 2000" (German Offenlegungschrift 3,009,755) | 220 | 18.8 not dimensionally stable! |
| A (present invention) | 66 | 30.8 |

While the prior art processes effect only minor increase in the abrasion resistance and no change in the flexural strength, the process of the present invention brings about an increased flexural strength and a highly increased resistace to abrasion.

EXAMPLE 6 (COMPARATIVE TEST)

In the following Table 3 the specific scelerometric volume loss (determined as described in Example 4) and the flexural strength (determined as described in Example 5) of a series of commercial hard plaster products are listed which were tested both without curing, and another time after curing with solution A (see Examples 4 and 5). Moreover, the resistance to pressure was determined on test pieces of 2×2×4 mm size which had been treated analogous to the flexural strength bars according to Example 5.

TABLE 3

| Tested Plaster | Specific Sclerometric Volume Loss per 1 cm Groove Length [mm³ × 10⁻³] | Flexural Strength [MPa] | Resistance to Pressure [MPa] |
|---|---|---|---|
| Kaffir D⁺ (Kaffir) | | | |
| untreated | 728 | 20.8 | 54.7 |
| treated with solution A of invention | 88 | 30.8 | 123.3 |
| Moldano⁺ (Bayer) | | | |
| untreated | 225 | 20.1 | 46.7 |
| treated with solution A of invention | 69 | 28.5 | 76.0 |
| Vel-Mix-Stone⁺ (Kerr) | | | |
| untreated | 487 | 27.9 | 84.3 |
| treated with solution A of invention | 45 | 32.7 | 129.5 |
| Duroc⁺ (Ransom + Randolph) | | | |
| untreated | 245 | 19.0 | 59.3 |
| treated with solution A of invention | 66 | 30.8 | 86.2 |
| Begolith⁺ (Bego) | | | |
| untreated | 51 | 29.0 | 110.5 |
| treated with solution A of invention | 42 | 38.6 | 134.1 |

⁺tradename

EXAMPLE 7 (COMPARATIVE TEST)

Test pieces prepared from commercial molding plaster (tradename "Moldano" manufactured by Bayer) for measuring the specific sclerometric volume loss per 1 cm groove length, the flexural strength, and the resistance to pressure (see Example 6) are first stored for 24 hours in standard climate (see Example 4) and then treated as follows, before the measurements:

I no further pretreatment

II according to the invention with solution A, as described in Example 6

III The test pieces are immersed into a solution of 10% by weight of benzoyl peroxide and 90% by weight of acetone for 15 seconds. After drying for 5 minutes, the test pieces are then immersed in a monomer mixture of 47% by weight Bis-GMA (reaction product of bisphenol A and glycidyl methacrylate) and 51% by weight of triethylene glycol dimethacrylate (containing 2% by weight of N,N-diethanol-p-toluidine) for 100 seconds. Thereafter the test pieces are wiped with acetone (see European Patent Publication No. 0,013,354, Example 1).

IV Ten drops of the monomer mixture of III (containing 2% by weight of N,N-diethanol-p-toluidine) are mixed with 10 drops of said monomer mixture (containing 2% by weight of benzoyl peroxide). The mixture is applied onto the test pieces with a brush. After 1 minute the excess is wiped off (see European Patent Publication No. 0,013,354, Example 1, last paragraph).

The results of the measurements are compiled in Table 4.

TABLE 4

| Pretreatment | Specific Sclerometric Volume Loss per 1 cm Groove Length [mm³ × 10⁻³] | Flexural Strength [MPa] | Resistance to Pressure [MPa] |
|---|---|---|---|
| I | 225 | 20.1 | 46.7 |
| II | 69 | 28.5 | 76.0 |
| III | 108 | 17.8 | 68.6 |
| IV | 121 | 20.3 | 58.6 |

Only the test pieces pretreated according to I and II are dimensionally stable. The flexural strength is improved only by the process of the invention. There is a distinct improvement of resistance to abrasion and to pressure, as compared with the process of European Patent Publication No. 0,013,354.

What is claimed is:

1. A process for producing plaster models for use in dentistry which possess an improved resistance to abrasion, bending and pressure which comprises
   impregnating a plaster model with (a) at least one photopolymerizable ester of acrylic and/or methacrylic acid and (b) at least one photopolymerization initiator and
   irradiating the impregnated plaster model with light suited for initiating the photopolymerization by the photoinitiator.

2. The process of claim 1 wherein the plaster model is additionally impregnated with (c) at least one photopolymerization activator.

3. The process of claim 1 wherein components (a) and (b) are present in a liquid or dissolved state.

4. The process of claim 2 wherein components (a), (b) and (c) are present in a liquid or dissolved state.

5. The process of claim 1 wherein component (b) and at least a portion of component (a) are employed in the form of a mixture.

6. The process of claim 2 wherein components (b), (c) and at least a portion of component (a) are employed in the form of a mixture.

7. The process of claim 2 wherein the components (a), (b) and (c) and mixtures and solutions thereof have a viscosity of up to about 5 poises.

8. The process of claim 1 wherein component (a) includes urethane acrylates and methacrylates.

9. The process of claim 1 wherein component (a) is selected from the group consisting of mono-, di-, and polyfunctional acrylates and methacrylates.

10. The process of claim 1 wherein the monofunctional derivatives are methyl methacrylate and hydroxyethyl methacrylate.

11. The process of claim 1 wherein the photopolymerization initiator is selected from the group consisting of aromatic monoketones, aromatic and aliphatic 1,2-diketones, thioxanthones, benzoine ethers, benzil ketals and mixtures thereof.

12. The process of claim 11 wherein the photopolymerization initiator is present in an amount of about 0.01 to 3% by weight, based on component (a).

13. The process of claim 2 wherein the photoactivator is selected from the group consisting of tertiary amines, cyclic 1,3-diketones and organic phosphites.

14. The process of claim 1 further including the addition of (d) an organic peroxide or hydroperoxide and (e) aromatic amines or thiourea derivatives as an activator therefor.

15. A process for producing a plaster model for use in dentistry which possesses an improved resistance to abrasion, bending and pressure which comprises
   impregnating a plaster model with (a) at least one photopolymerizable ester of acrylic and/or methacrylic acid and (b) at least one photopolymerization initiator, said impregnation being conducted for a period of time sufficient to provide a penetration depth of component (a) into the plaster model of at least 0.1 mm, and
   irradiating the impregnated plaster model with light suited for initiating the photopolymerization by the photoinitiator.

16. A process according to claim 15, wherein said penetration depth of component (a) is at least 0.5 mm.

* * * * *